United States Patent [19]

Tate et al.

[11] Patent Number: 5,276,172
[45] Date of Patent: Jan. 4, 1994

[54] METAL ORGANIC COMPOUNDS

[75] Inventors: Philip E. R. Tate, Hazel Grove; John W. Prince, Whitworth; John M. Hilton, Bramley Cross, all of United Kingdom

[73] Assignee: Rhone-Poulenc Chemicals Ltd., London, United Kingdom

[21] Appl. No.: 727,111

[22] Filed: Jul. 9, 1991

[30] Foreign Application Priority Data

Jul. 10, 1990 [GB] United Kingdom ............... 9015150

[51] Int. Cl.$^5$ ............................................. C07F 5/02
[52] U.S. Cl. ...................................... 556/28; 556/30; 556/31; 556/7; 556/13; 556/24; 106/244; 106/245; 106/268; 106/270
[58] Field of Search ............... 556/7, 13, 24, 28, 30, 556/31

[56] References Cited

U.S. PATENT DOCUMENTS

| | | | |
|---|---|---|---|
| 4,234,496 | 11/1980 | Harson | 556/13 |
| 4,588,766 | 5/1986 | Tate . | |
| 4,609,499 | 9/1986 | Esashi et al. | 556/7 |

FOREIGN PATENT DOCUMENTS

| | | |
|---|---|---|
| 0102023 | 3/1984 | European Pat. Off. . |
| 0148782 | 7/1985 | European Pat. Off. . |
| 0150840 | 8/1985 | European Pat. Off. . |
| 972804 | 10/1964 | United Kingdom . |
| 2022087A | 12/1979 | United Kingdom . |

Primary Examiner—Melvyn I. Marquis
Assistant Examiner—Mark Sweet
Attorney, Agent, or Firm—Finnegan, Henderson, Farabow, Garrett & Dunner

[57] ABSTRACT

Metal organic compounds comprising three atoms of cobalt, nickel or bismuth each linked through oxygen atoms to boron or phosphorus and comprising a combination of aliphatic and aromatic carboxylic acid residues are useful as adhesion promoters to promote the adhesion of brass-coated steel to vulcanised rubber.

5 Claims, No Drawings

METAL ORGANIC COMPOUNDS

This invention relates to metal organic compounds, compositions containing them, and their use.

Compounds comprising three atoms of a divalent metal, e.g. cobalt, each linked through oxygen atoms to a boron or phosphorus atom and comprising aliphatic monocarboxylic acid residues bonded to the metal are known. Such known compounds have been used as additives to rubber skim stock to improve adhesion of the rubber to metal.

They are provided in a form which is readily handleable, and in particular is not inherently tacky or viscous.

The present invention provides new compounds which have the advantages of the aforesaid known compounds, but which improve still further the adhesion of rubber to brass-coated steel cord and the retention of such adhesion under conditions of steam and salt ageing, when compared to the known cobalt-containing compounds.

According to the present invention there are provided metal-organic compounds for use in promoting adhesion of rubber to metal, of average formula:

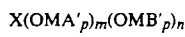

in which:
X is boron

phosphorus

or phosphorus bonded to an oxo oxygen

M is cobalt, nickel, or bismuth;
B' is an aromatic carboxylic acid residue of 7 to 11 carbon atoms;
A' is an aliphatic carboxylic acid residue of 7 to 11 carbon atoms;
p is 1 when M is cobalt or nickel or 2 when M is bismuth;
n is 0.5 to 2, preferably 0.5 to 1.5, and m is (3−n).

The aliphatic carboxylic acid (A'—H) is preferably a monocarboxylic acid, e.g. n-heptanoic acid, 2,2-dimethylpentanoic, acid, 2-ethylpentanoic acid, 2-ethylpentanoic acid, 4,4-dimethylpentanoic acid, n-octanoic acid, 2,2-dimethylhexanoic acid, 2-ethylhexanoic acid, 4,4-dimethylhexanoic acid, 2,4,4-trimethylpentanoic acid, n-nonanoic acid, 2,2-dimethylheptanoic acid, 6,6-dimethylheptanoic acid, 3,5,5-trimethylhexanoic acid, n-decanoic acid, 2,2-dimethyloctanoic acid, 7,7-dimethyloctanoic acid, n-undecanoic acid, or the mixture of 2,2,2-trialkyl acetic acids known as neodecanoic or versatic acid.

The aromatic carboxylic acid (B'—H) may be, for example, benzoic acid, an alkyl-, alkoxy-, amino-, halogen-, thio-, or hydroxy-substituted benzoic acid, such as salicylic acid, anthranilic acid, or 4-chloro-benzoic acid, phthalic acid, terephthalic acid, cinnamic acid, or a more complex aromatic acid comprising a conjugated ring system.

The metal-organic compound may be associated with a borate of an element of group IA or IIA of the Periodic Table (i.e. an alkali metal or an alkaline earth metal). Said borates may be present at a concentration of up to 20% by weight of the metal organic compound. Suitable borates include sodium borate, potassium borate, calcium borate and magnesium borate.

The metal organic compound may also be associated with microcrystalline wax and/or process oil.

The novel metal organic compounds may be incorporated as adhesion promoters in rubber skim stock comprising rubber and conventional rubber compounding ingredients. The metal-organic compound may be present in an amount between 0.2 and 2 parts by weight per hundred parts by weight of rubber, and preferably the metal-organic compound provides about 0.224 parts by weight of cobalt metal per hundred parts by weight of rubber.

The metal organic compounds of the present invention may be made by heating together a mixture in the required proportions of (1) the acids A'H and B'H which give rise to the residues A' and B' as defined above, (2) a source of the metal M such as in particular an oxide, hydroxide or carbonate of that metal, (3) a borate, phosphite or phosphate ester of a lower alcohol, e.g. n-butanol, and (4) an acid capable of forming a volatile ester with the lower alcohol residues present in the said borate, phosphite or phosphate ester, e.g. acetic acid or propionic acid, and distilling off the said volatile ester, preferably under reduced pressure. All of the acids (1) and (4) and the metal source (2) must be pre-reacted before the ester (3) is added. The reaction temperature is typically in the range 50° to 250° C.

The invention is illustrated by the following Examples. Examples 1 to 26 describe the preparation of the new metal organic compounds.

EXAMPLE 1

Neodecanoic acid (210 g), propionic acid (147 g) and xylene (300 g) were charged to a reaction flask and heated at 50° C. with mechanical stirring. Cobaltous hydroxide (171 g) was added and the temperature raised to 90° C. with mechanical stirring to produce a mobile blue liquid. Further heat was applied to remove water of reaction via xylene entrainment using a Dean & Stark trap. When the temperature had reached 140° C., benzoic acid (73 g) dissolved in xylene (150 g) was gradually added to the reaction mixture while the water formed was continuously removed. After completion of water removal (65 g) the xylene was removed by short path distillation to a maximum temperature of 155° C. using vacuum to complete the removal. n-Butyl orthoborate (138 g) was added. The reaction mixture was heated to 190° C. and refluxed for three hours. n-Butyl propionate (220 g) was then distilled off at a maximum temperature of 220° C. with vacuum to complete the ester removal.

The product (437 g) was a hard blue solid of average formula:

B(OCoB') (OCoA')₂

Where A'=neodecanoate and B'=benzoate

EXAMPLE 2

Neodecanoic acid (29.4 k9) and xylene (14.5 kg) were charged to a reaction vessel and heated with stirring to 90° C. Cobaltous hydroxide (20.6 kg) was added and allowed to slurry with mechanical stirring for 15 minutes. Propionic acid (17.6 kg) was added and the batch was kept at 90° C. for 30 minutes. Heat was then applied to remove water of reaction via distillation. When the temperature reached 130° C. benzoic acid (6 kg) was added. The reaction was continued to a temperature of 190° C. and the water of reaction (7.9 kg) and xylene (14.5 kg) were removed by vacuum distillation. n-Butyl orthoborate (18.6 kg) was added and the batch kept overnight at 160° C. The temperature was then raised to 220° C. and n-butyl propionate (28 kg) was distilled off over a period of six hours with a vacuum in the final stages. A hard blue solid product (52 kg) was obtained.

EXAMPLE 3

A solution of cobalt neodecanoate propionate (800 g) at 10% (w/w) cobalt in mineral spirits was heated to 50° C. with mechanical stirring. Propionic acid (50 g) and benzoic acid (83 g) were added. The reaction mass was mixed for 10 minutes and cobaltous hydroxide (65 g) was then added. The reaction mixture was heated to 190° C. and water (24 g) and mineral spirits (380 g) were distilled off. n-Butyl orthoborate (157 g) was added and the reaction mixture heated under reflux at 180° C. for one hour. n-Butyl propionate (250 g) was then removed by distillation at a maximum temperature of 230° C., vacuum being used to complete the ester distillation.

The product (497 g) was a hard blue solid of average formula:

B(OCoB') (OCoA')₂

Where A'=neodecanoate and B'=benzoate

EXAMPLES 4-26

Aliphalic carboxylic acid A (1-2 mole), aromatic carboxylic acid B (0-1 mole) and either propionic acid (1 mole) or acetic acid (1 mole) together with xylene, were charged to a reaction flask and heated to 50° C. with stirring. An addition of a metal (cobalt, bismuth or nickel) oxide, hydroxide or carbonate (1.0 mole) was made and the mixture was heated to remove water of reaction via xylene entrainment using a Dean & Stark trap. When the water formed by the reaction had been removed, the xylene was removed by short path distillation to a maximum temperature of 180° C. using vacuum to complete the removal. Either n-butyl orthoborate (0.33 mole) or tri(n-butyl)phosphate (0.33 mole) was added and the reaction mixture was heated under reflux for three hours before the ester (1.0 mole) was removed by distillation to a maximum temperature of 230° C., again using vacuum to complete the distillation.

The reaction products are hard solids of the average general formula:

$$X(OMA'_p)_m (OMB'_p)_n$$

X=boron or phosphorus bonded to an oxo oxygen
M=cobalt, bismuth or nickel
p=1 or 2
A=aliphatic acid residue
B=aromatic acid residue and the ratio of m to n is shown in the Table as the ratio of A:B.

In addition a selected number of compounds were:
(1) Dissolved in process oil to give solutions at 16% cobalt. This produced mobile, intense blue solutions.
(2) Dispersed with paraffin wax at levels of 10-20% wax. This has the effect of reducing brittleness and further reducing any tendency to form dust.
(3) Dissolved in mineral spirits to give low viscosity intense blue solutions.

The compounds prepared in this way are shown in the following list.

| Example | Metal | Metal Content of Product (%) | Borate/ Phosphate | Acids A | B | Ratio A:B | Physical Appearance |
|---|---|---|---|---|---|---|---|
| | | | | EXAMPLES 4-26 | | | |
| Example 4 | Cobalt | 22.8 | Borate | Neodecanoic | Salicylic | 2.5:0.5 | Dark blue, brittle solid. |
| Example 5 | Cobalt | 22.8 | Borate | Neodecanoic | Salicylic | 2.0:1.0 | Dark blue, brittle solid. |
| Example 6 | Cobalt | 22.0 | Borate | Neodecanoic | Anthranilic | 2.5:0.5 | Brittle, matt, blue solid. |
| Example 7 | Cobalt | 22.6 | Borate | Neodecanoic | Anthranilic | 2.0:1.0 | Brittle, matt, blue solid. |
| Example 8 | Cobalt | 21.8 | Borate | Neodecanoic | Cinnamic | 2.5:0.5 | Dark blue, glossy, brittle solid. |
| Example 9 | Cobalt | 22.9 | Borate | Neodecanoic | Cinnamic | 2.0:1.0 | Dark blue, matt, brittle solid. |
| Example 10 | Cobalt | 24.4 | Borate | Neodecanoic | Terephthalic | 2.5:0.5 | Very hard, dark blue solid. |
| Example 11 | Cobalt | 24.2 | Borate | Neodecanoic | Terephthalic | 2.0:1.0 | Very hard, dark blue solid. |
| Example 12 | Cobalt | 24.2 | Borate | Neodecanoic | Phthalic | 2.5:0.5 | Dark blue, glossy, brittle solid. |
| Example 13 | Cobalt | 26.8 | Borate | Neodecanoic | Phthalic | 2.0:1.0 | Dark blue, very hard, brittle solid. |
| Example 14 | Cobalt | 21.6 | Borate | Neodecanoic | 4-Chlorobenzoic | 2.5:0.5 | Dark blue solid. |
| Example 15 | Cobalt | 22.5 | Borate | Neodecanoic | 4-Chlorobenzoic | 2.0:1.0 | Dark blue, brittle solid. |
| Example 16 | Cobalt | 23.9 | Phosphate | Neodecanoic | Benzoic | 2:1 | Hard, brittle, dark blue solid. |
| Example 17 (16 + oil) | Cobalt | 16.0 | Phosphate | Neodecanoic | Benzoic | 2:1 | Solution of 16 in process oil. Viscous, blue solution. |
| Example 18 (16 + wax) | Cobalt | 20 | Phosphate | Neodecanoic | Benzoic | 2:1 | Sample 16 with the addition of 20% paraffin wax. Clean breaking, non-dusty, blue solid. |
| Example 19 | Cobalt | 23.5 | Borate | Iso-undecanoic | Benzoic | 2.5:0.5 | Very hard, dark blue, brittle solid. |
| Example 20 (19 + wax) | Cobalt | 21.4 | Borate | Iso-undecanoic | Benzoic | 2.5:0.5 | Sample 19 + 10% wax. Hard, clean breaking, non-dusty, blue solid. |
| Example 21 (19 + oil) | Cobalt | 16.0 | Borate | Iso-undecanoic | Benzoic | 2.5 0.5 | Mobile blue solution |
| Example 22 | Cobalt | 26.8 | Borate | 2-ethyl hexoic | Benzoic | 2.5:0.5 | Very hard, brittle, dark blue solid. |

-continued

| Example | Metal | Metal Content of Product (%) | Borate/ Phosphate | Acids A | B | Ratio A:B | Physical Appearance |
|---------|-------|------------------------------|-------------------|---------|---|-----------|---------------------|
| Example 23 (22 + oil) | Cobalt | 16.0 | Borate | 2-ethyl hexoic | Benzoic | 2.5:0.5 | Mobile, viscous, blue solution in process oil. |
| Example 24 (22 + wax) | Cobalt | 24.4 | Borate | 2-ethyl hexoic | Benzoic | 2.5:0.5 | Sample 22 + 10% paraffin wax. Clean breaking, non-dusty solid. |
| Example 25 | Bismuth | 39.5 | Borate | Neodecanoic | Benzoic | 2:1 | Opaque, buff solid. |
| Example 26 | Nickel | 20.7 | Borate | Neodecanoic | Benzoic | 2.25:0.75 | Very hard, brittle, dark green solid. |

Rubber skim stock in accordance with the present invention comprises rubber plus conventional rubber compounding ingredients such as pigments, fillers, extenders, accelerators, antioxidants, vulcanising agents, etc. and, as an adhesion promoter, a metal-organic compound of the present invention.

A rubber skim stock was prepared having the following composition:

| | Parts by Weight |
|---|---|
| Natural Rubber SMR 10 | 100.00 |
| Peptiser (P.C.T.P.)[a] | 0.12 |
| HAF Carbon Black N-326 | 55.00 |
| Zinc oxide | 8.00 |
| Stearic acid | 0.5 |
| Highly Aromatic Process Oil | 3.00 |
| Antidegradant (6 pPD)[b] | 2.00 |
| Accelator (DCBS)[c] | 0.7 |
| Insoluble Sulphur | 4 |

[a] Zinc salt of pentachlorothiophenol
[b] N-(1,3-dimethylbutyl)-N'-phenyl-p-phenylene diamine
[c] N,N-Dicyclohexyl-2-benzthiazyl sulphenamide.

Vulcanisable compositions were prepared using the above rubber skim stock and the adhesion promoters listed below.

| Adhesion Promoter | Parts per hundred parts of rubber | Cobalt concentration (parts per 100 parts of rubber) |
|---|---|---|
| Cobalt Stearate | 1.58 | 0.15 |
| Manobond C22.5 | 0.67 | 0.15 |
| Example 3 | 0.64 | 0.15 |
| Example 16 | 0.66 | 0.15 |
| Example 6 | 0.66 | 0.15 |
| Example 7 | 0.68 | 0.15 |
| Example 11 | 0.61 | 0.15 |

The adhesion promoters were added to the skim stock during mixing in a 1.5 liter laboratory internal mixer and sheeted off on a 2-roll laboratory mill. All the compositions were vulcanised to $T_{90}$+six minutes at 153° C.

Adhesion tests were carried out using a modified static block pull test based upon ASTM D2229 using an embedment length of 10 mm. Typical brass coated steel tire cord of the construction 2+2×0.25 from Bekaert was used, each cord having a coating of brass with an average copper content of 63.5%. Adhesion values are quoted in Newtons/10 mm. The results are given in Table 1.

TABLE 1

| | ADHESION (N/10 mm) AFTER VULCANIZATION TO $T_{90}$ + MINS @ 153° C. | | | | |
|---|---|---|---|---|---|
| PROMOTER | UNAGED | STEAM AGED | HUMIDITY | HEAT AGED | SALT WATER AGED |
| None | 240 [5] | 280 [8] | 330 [8] | 180 [5] | 140 [4] |
| Cobalt Stearate | 390 [9] | 260 [7] | 330 [8] | 330 [8] | 200 [6] |
| Cobalt Boro Neodecanoate[a] | 390 [9] | 23 [7] | 370 [8] | 330 [8] | 210 [5] |
| Product of Example 3 | 440 [10] | 290 [7] | 390 [9] | 340 [8] | 227 [5] |
| Product of Example 15 | 380 [9] | 260 [7] | 310 [7] | 270 [7] | 75 [3] |
| Product of Example 5 | 400 [9] | 330 [8] | 400 [9] | 300 [8] | 170 [4] |
| Product of Example 6 | 440 [10] | 290 [7] | 390 [9] | 350 [9] | 240 [5] |
| Product of Example 10 | 380 [9] | 260 [7] | 310 [9] | 240 [8] | 130 [3] |

Figures in parenthesis [ ] indicate wire coverage on a scale 1–10 (10 being best).
Ageing Conditions
Steam 16 hours @ 121° C.
Humidity 7 days @ 70° C. 95% R.H.
Heat 7 days @ 85° C.
Salt 7 day @ R.T. 10% sea water solution
[a] = Manobond C22.5 (Manobond is a registered trade name of Rhône-Poulenc Chemicals Ltd.)

The samples were further tested for fatigue to failure in kilocycles at 100% extension of the rubber using a Monsanto Fatigue to Failure tester. Results are shown in Table 2.

TABLE 2

| PROMOTER | FATIGUE TO FAILURE TESTING (KILOCYCLES TO FAILURE) |
|---|---|
| None | 155 |
| Cobalt Stearate | 141 |
| Cobalt Boro Neodecanoate[a] | 151 |
| Product of Example 3 | 162 |
| Product of Example 15 | 165 |
| Product of Example 5 | 175 |
| Product of Example 6 | 199 |
| Product of Example 10 | 170 |

[a] = Manobond C22.5 (Manobond is a registered Trade name of Rhône-Poulenc Chemicals Ltd.)

The results given in these Tables shows that rubber skim stock comprising the metal-organic compounds of the present invention exhibits substantially improved fatigue to failure and improvements in adhesion of rubber to metal under steam aged, salt aged and control conditions in comparison with rubber skim stock comprising known metal-organic compounds.

We claim:
1. A metal organic compound of the formula:
   $X(OMA'_p)_m(OMB'_p)_n$ wherein X is

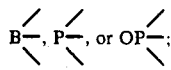

M is cobalt, nickel, or bismuth;
B' is a radical of an aromatic carboxylic acid of 7 to 11 carbon atoms;
A' is a radical of an aliphatic carboxylic acid of 7 to 11 carbon atoms;
p is 1 when M is cobalt or nickel or 2 when M is bismuth;
n is 0.5 to 2; and
m is $(3-n)$.

2. A metal organic compound according to claim 1 in which X is $$B\!\!-\!\!\genfrac{}{}{0pt}{}{\diagup}{\diagdown}$$

and M is cobalt (II).

3. A metal organic compound according to claim 1 in which B' is a radical of benzoic acid, salicylic acid, anthranilic acid, cinnamic acid, phthalic acid, terephthalic acid, or 4-chlorobenzoic acid, A' is a radical of neodecanoic acid, isoundecanoic acid, or 2-ethylhexanoic acid, n is 0.5 to 1.5 and m is 2.5 to 1.5.

4. A metal organic compound as claimed in claim 1, associated with up to 20% by weight of a borate of a metal of Group IA or IIA of the Periodic Table.

5. A metal organic compound as claimed in claim 1, associated with microcrystalline wax and/or process oil.

* * * * *